(12) United States Patent
Himmler et al.

(10) Patent No.: US 8,785,673 B2
(45) Date of Patent: Jul. 22, 2014

(54) METHOD FOR PRODUCING 2-CHLOROALLYL THIOCYANATE AND 2-CHLOROALLYL ISOTHIOCYANATE

(75) Inventors: Thomas Himmler, Odenthal (DE); Matthias Decker, Köln (DE); Ralf Dunkel, Leichiingen (DE); Peter Gerdes, Aachen (DE); Martin Littmann, Leverkusen (DE); Norbert Lui, Odenthal (DE); Albert Schnatterer, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/113,739

(22) PCT Filed: Apr. 24, 2012

(86) PCT No.: PCT/EP2012/057431
§ 371 (c)(1),
(2), (4) Date: Dec. 19, 2013

(87) PCT Pub. No.: WO2012/146569
PCT Pub. Date: Nov. 1, 2012

(65) Prior Publication Data
US 2014/0107367 A1    Apr. 17, 2014

(30) Foreign Application Priority Data
Apr. 26, 2011 (EP) ..................................... 11163718

(51) Int. Cl.
*C07C 331/22*    (2006.01)
(52) U.S. Cl.
USPC ........................................................ 558/19

(58) Field of Classification Search
USPC ........................................................ 558/19
See application file for complete search history.

(56) References Cited

FOREIGN PATENT DOCUMENTS

| CN | 1401646 | 3/2003 |
|---|---|---|
| EP | 0446913 | 9/1991 |
| EP | 0761649 | 3/1997 |
| ZA | 753527 | 4/1976 |

OTHER PUBLICATIONS

Dai et al., Synthesis and Biological Activities of Novel Pyrazole Oxime Derivatives Containing a 2-Chloro-5-thiazolyl Moiety, 2008, J. Agric. Food Chem., 56, 10805-10810.*
International Search Report for PCT/EP2012/057431 Mailed July 19, 2012.
Wenzheng et al. "Research on Synthetic Methods of Thiamethoxam," vol. 27 (2002) pp. 25-27.
Dai et al. "Synthesis and Biological Activities of Novel Pyrazole Oxime Derivatives Containing a 2-Chloro-5-Thiazolyl Moiety," J. Agric. Food Chem, vol. 56 (2008) pp. 10805-10810.
Wang et al. "Synthesis and Herbicidal Activity of 2-Cyano-3-(2-Chlorothiazol-5-Yl) Methylaminoacrylates," J. Agric. Food Chem., vol. 52 (2004) pp. 1918-1922.

* cited by examiner

*Primary Examiner* — Kristin Vajda
(74) *Attorney, Agent, or Firm* — Miles & Stockbridge, P.C.

(57) ABSTRACT

A process is described for producing 2-chloroallyl isothiocyanate from 2,3-dichloro-1-propene by reacting the 2,3-dichloro-1-propene with a thiocyanate in the presence of a phase transfer catalyst, without diluent or in the presence of up to 15 percent by weight based on 2,3-dichloropropene and simultaneously in the presence of an excess of from 10 to 200 mol percent of 2,3-dichloro-1-propene based on the thiocyanate. A process starting from 1,2,3-trichloropropane is also described.

6 Claims, No Drawings

METHOD FOR PRODUCING 2-CHLOROALLYL THIOCYANATE AND 2-CHLOROALLYL ISOTHIOCYANATE

CROSS REFERENCE TO RELATED APPLICATIONS

This application is a §371 National Stage Application of PCT/EP2012/057431, filed Apr. 24, 2012, which claims priority to European Application No. 11163718.7, filed Apr. 26, 2011.

BACKGROUND OF THE INVENTION

1. Field of the Invention

The present invention relates to a process for producing 2-chloroallyl thiocyanate of the formula (I) and 2-chloroallyl isothiocyanate of the formula (II).

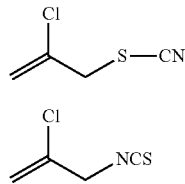

2-Chloroallyl thiocyanate of the formula (I) is a known compound (see by way of example EP 0761649). It is also known that 2-chloroallyl thiocyanate of the formula (I) can be produced by reacting, in a diluent, a 2,3-dihalo-1-propene, preferably 2,3-dichloro-1-propene of the formula (III)

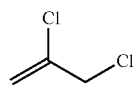

with a thiocyanate of the general formula (IV)

$$M(SCN)_n \quad (IV),$$

in which

M is a metal cation or an ammonium group and n is from 1 to 4, as appropriate for the charge number of the cation.

2. Description of Related Art

An example of a suitable diluent described for the known processes is acetonitrile (EP 446913; CN 1401646) or toluene, optionally with addition of a phase transfer catalyst (Shanghai Huagong 27 (2002) 25-27; J. Agric. Food Chem. 56 (2008) 10805-10810). However, the use of these diluents is disadvantageous for an industrial process. By way of example, the dilution of the starting materials can markedly reduce the reaction rate and thus prolong the reaction time required. The use of a diluent also unavoidably implies additional work-up steps. By way of example, distillation is required to remove the diluent, and care has to be taken here that the purity of the reclaimed diluent is sufficient to permit its return to the process. Otherwise there is a need for expensive disposal, which may cause pollution of the environment.

This also applies to the known use of water as diluent (EP 0761649; J. Agric. Food Chem. 52 (2004) 1918-1922). Here, the process is carried out in a mixture of two liquid phases (water and organic phase) in the presence of a phase transfer catalyst. There can then sometimes be considerable amounts of wastewater requiring disposal.

It is likewise known that the 2-chloroallyl thiocyanate of the formula (I) undergoes rearrangement at temperatures above room temperature to give 2-chloroallyl isothiocyanate of the formula (II) (EP 446913; EP 761649; J. Agric. Food Chem. 52 (2004) 1918-1922). When 2-chloroallyl thiocyanate of the formula (I) is obtained from 2,3-dichloro-1-propene of the formula (III) and from a thiocyanate of the formula (IV), mixtures of the compounds of the formulae (I) and (II) are therefore generally obtained. In industrial processes, this mixture is usually converted entirely to the 2-chloroallyl isothiocyanate of the formula (II) by heating, for example during distillative work-up. The overall process can accordingly be illustrated by the following diagram:

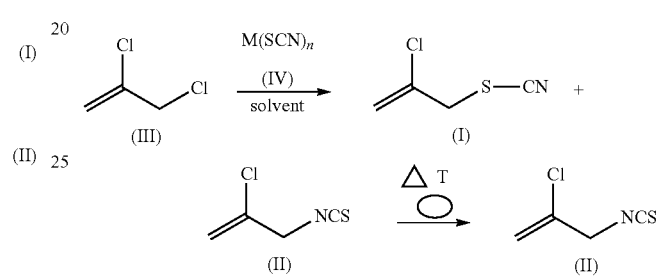

2-Chloroallyl isothiocyanate of the formula (II) is used by way of example as intermediate in producing plant-protection compositions (EP 446913).

There was therefore a continuing requirement for a further-improved process for producing 2-chloroallyl thiocyanate of the formula (I) and 2-chloroallyl isothiocyanate of the formula (II) under conditions that are advantageous in industry.

SUMMARY

Surprisingly, a novel process has now been discovered for producing 2-chloroallyl thiocyanate of the formula (I) and 2-chloroallyl isothiocyanate of the formula (II), characterized in that 2,3-dichloro-1-propene of the formula (III)

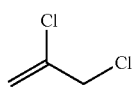

is reacted with a thiocyanate of the general formula (IV), $$M(SCN)_n \quad (IV),$$

in which

M is a metal cation or an ammonium group and n is from 1 to 4, as appropriate for the charge number of the cation, in the presence of a phase transfer catalyst of the general formula (V),

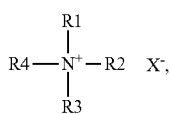

in which the moieties

R$^1$, R$^2$, R$^3$ and R$^4$ are mutually independently hydrogen, C$_1$-C$_{24}$-alkyl, benzyl or C$_6$-C$_{10}$-aryl, the latter optionally substituted by halogen, C$_1$-C$_6$-alkyl, C$_1$-C$_6$-alkoxy, C$_1$-C$_6$-alkylamino, C$_1$-C$_6$-dialkylamino, hydroxy or phenyl and X is an anion, without diluent or in the presence of only a very small amount of diluent of up to 15 percent by weight, based on 2,3-dichloropropene of the formula (III) and simultaneously in the presence of an excess of from 10 to 200 mol percent of 2,3-dichloro-1-propene of the formula (III) based on the thiocyanate of the formula (IV).

DETAILED DESCRIPTION OF A PREFERRED EMBODIMENT

Diluents that can optionally be used comprise polar and nonpolar organic diluents, and also water. Examples that may be mentioned are hydrocarbons, such as toluene, xylenes, hexane, heptane, methylcyclohexane; halogenated hydrocarbons, such as dichloromethane, 1,2-dichloroethane; alcohols, such as methanol, ethanol, propanol, isopropanol, butanol; esters, such as methyl acetate, ethyl acetate, butyl acetate; ketones, such as acetone, methyl ethyl ketone, methyl isobutyl ketone, and nitriles, such as acetonitrile, butyronitrile, isobutyronitrile.

It is preferable to carry out the process according to the invention by reacting 2,3-dichloro-1-propene of the formula (III)

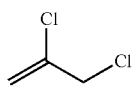

with a thiocyanate of the general formula (IV)

M(SCN)$_n$      (IV), in which

M is Li$^+$, Na$^+$, K$^+$ or NH$_4^+$ and n is 1, in the presence of a phase transfer catalyst of the general formula (V)

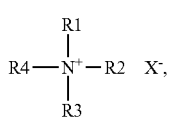

in which the moieties

R$^1$, R$^2$, R$^3$ and R$^4$ are mutually independently hydrogen, C$_1$-C$_{24}$-alkyl, benzyl or phenyl and X is an anion from the group of fluoride, chloride, bromide, hydrogensulphate, hydroxide or acetate, in the presence of an amount of from 0 to 10 percent by weight, based on 2,3-dichloro-1-propene of the formula (III), of diluent, and simultaneously in the presence of an excess of from 10 to 200 mol percent of 2,3-dichloro-1-propene of the formula (III), based on the thiocyanate of the formula (IV).

Diluents that can optionally be used with preference comprise toluene, methylcyclohexane, dichloromethane, methanol, ethanol, propanol, isopropanol, butanol, methyl acetate, ethyl acetate, butyl acetate, acetone, methyl ethyl ketone, methyl isobutyl ketone, acetonitrile, butyronitrile, isobutyronitrile and also water.

It is preferable not to add any further diluent to the reaction. The total amount of diluent is then the sum of the diluent contents of the starting materials of the formula (III), and also of the thiocyanate. The said total amount is usually below 10 percent by weight, or preferably below 5 percent by weight, based on the compound of the formula (III).

The process according to the invention is particularly preferably carried out by reacting 2,3-dichloro-1-propene of the formula (III)

with a thiocyanate of the general formula (IV)

M(SCN)$_n$      (IV), in which

M is Na$^+$ or NH$_4^+$ and n is 1, in the presence of a phase transfer catalyst of the general formula (V)

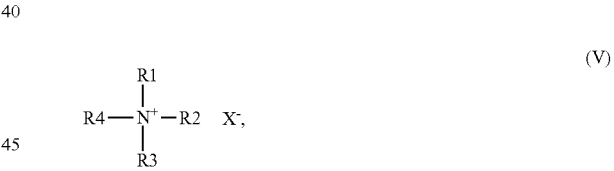

in which the moieties

R$^1$, R$^2$, R$^3$ and R$^4$ are mutually independently hydrogen, C$_1$-C$_{24}$-alkyl, benzyl or phenyl and X is an anion from the group of chloride, bromide, hydrogensulphate or hydroxide, in the presence of an amount of from 0 to 5 percent by weight, based on 2,3-dichloro-1-propene of the formula (III), of diluent, and simultaneously in the presence of an excess of from 30 to 100 mol percent of 2,3-dichloro-1-propene of the formula (III), based on the thiocyanate of the formula (IV).

Diluents optionally used with particular preference comprise toluene, dichloromethane, methanol, ethyl acetate, butyl acetate, acetone, methyl ethyl ketone, methyl isobutyl ketone, acetonitrile, butyronitrile, isobutyronitrile, and also water.

The process according to the invention has advantages over the known prior art. By way of example, the substantial omission of a diluent avoids the need for work-up and sometimes disposal of the same. At the same time, the space-time yield of the process according to the invention is higher than that of the processes corresponding to the known prior art.

The process according to the invention is carried out at temperatures of from 30 to 150° C. It is preferable to operate at temperatures of from 50 to 100° C.

The process according to the invention is usually carried out at atmospheric pressure, but can also be carried out at elevated or reduced pressure.

The reaction time in the process according to the invention is from 0.1 to 10 hours. It is preferable to use from 0.5 to 7 hours, particularly preferably from 1 to 5 hours.

The amount of phase transfer catalyst of the general formula (V) can be varied widely in the process according to the invention. Amounts usually used are from 0.1 to 10 percent by weight, based on 2,3-dichloro-1-propene of the formula (III). It is preferable to use amounts of from 1 to 7 percent by weight.

Examples of phase transfer catalysts of the general formula (V) that can be used are: tetrabutylammonium fluoride and the corresponding chloride, bromide, iodide, acetate, hydrogen-sulphate, tetraethylammonium bromide and the corresponding iodide, methyltributylammonium chloride and the corresponding bromide, iodide, acetate and hydrogensulphate, benzyldodecyldimethylammonium chloride and the corresponding bromide, benzyltriethylammonium bromide and the corresponding chloride, dodecyltrimethylammonium chloride and the corresponding bromide, tetradecyltrimethylammonium chloride and the corresponding bromide, methyltrioctylammonium chloride, methyltridecylammonium chloride, tetraoctylammonium bromide and the corresponding chloride, didecyldimethylammonium chloride and the corresponding bromide.

It is preferable to use methyltrioctylammonium chloride (trade mark Aliquat® 336; present in a mixture with methyltridecylammonium chloride), methyltridecylammonium chloride and the corresponding bromide, tetraoctylammonium bromide and the corresponding chloride, dodecyltrimethylammonium chloride and the corresponding bromide, tetradecyltrimethylammonium chloride and the corresponding bromide, didecyldimethylammonium chloride and the corresponding bromide and benzyldodecyldimethylammonium chloride or the corresponding bromide.

The addition of a phase transfer catalyst of the general formula (V) can optionally be omitted if the 2,3-dichloro-1-propene of the formula (III) used for the reaction has not been purified by distillation and therefore as a consequence of the industrial production process therefore already comprises an adequate amount of a phase transfer catalyst.

The usual method of producing the 2,3-dichloro-1-propene of the formula (III) reacts 1,2,3-trichloropropane of the formula (VI) with a base:

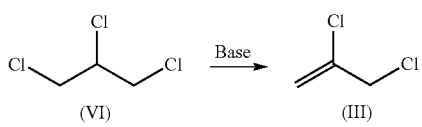

Bases that can be used here comprise organic and inorganic bases. An example that may be mentioned of an organic base is trimethylamine, triethylamine, tributylamine, pyridine, 5-ethyl-2-methylpyridine or quinoline. Examples of inorganic bases that can be used are alkali metal hydroxides, such as NaOH and KOH, alkaline earth metal hydroxides, such as Ca(OH)$_2$, alkali metal hydrogencarbonates, such as NaHCO$_3$ and KHCO$_3$, and alkali metal carbonates, such as Na$_2$CO$_3$, K$_2$CO$_3$ or Cs$_2$CO$_3$. In a typical method, a base is used, such as NaOH or KOH, and the process for producing 2,3-dichloro-1-propene of the formula (III) from 1,2,3-trichloropropane of the formula (VI) is carried out in water. This procedure gives a two-phase system, and a phase transfer catalyst is therefore added in order to achieve an adequate reaction rate. If the work-up of the 2,3-dichloro-1-propene of the formula (III) is then restricted to simple phase separation, the 2,3-dichloro-1-propene then comprises at least some of the phase transfer catalysts used for producing the same.

The mixture obtained where appropriate of 2-chloroallyl thiocyanate of the formula (I) and 2-chloroallyl isothiocyanate of the formula (II) can then be converted to the 2-chloroallyl isothiocyanate of the formula (II) by heating, for example in the context of distillative purification.

The examples below are intended to illustrate the process according to the invention, but there is no intention to restrict the process to these examples.

Example 1

Technical-grade 2,3-dichloro-1-propene (496.5 g) (GC analysis: 89.4% purity; water (KF): 0.45%) is used as initial charge in a 2-liter jacketed reaction vessel with stirrer and reflux condenser, and is heated to 70° C. At this temperature, 165.46 g of sodium thiocyanate (98% purity) are added in three portions, with stirring. The mixture is then heated to 80° C., and is stirred for 90 minutes at the said temperature, and cooled back to 70° C., and 500 ml of water are added. The organic phase is separated off at room temperature. This gives 530.3 g of organic phase, which according to GC analysis comprises 41.8 percent by area of 2,3-dichloro-1-propene, 24.9 percent by area of 2-chloroallyl thiocyanate of the formula (I) and 24.5 percent by area of 2-chloroallyl isothiocyanate of the formula (II).

This organic phase is distilled at 250 mbar until the bath temperature reaches 75° C. This gives 212.7 g of distillate with, according to GC analysis, 207.6 g of 2,3-dichloro-1-propene, which can be returned to the process.

The amount of residue after distillation is 313.6 g, and according to analysis by quantitative $^1$H NMR spectroscopy it is composed of 82.3 percent by weight of 2-chloroallyl thiocyanate of the formula (I) and 2-chloroallyl isothiocyanate of the formula (II), giving a yield of 97% of theory, based on sodium thiocyanate.

Example 2

Distilled 2,3-dichloro-1-propene (150 g) (GC analysis: 97.3% purity; water (KF): <0.1%) is mixed for 30 minutes with 6 g of Aliquat® 336 and 50 ml of water, and the phases are then separated. This pretreated 2,3-dichloro-1-propene (water (KF): 0.6%) is used as initial charge together with 333.3 g of technical-grade 2,3-dichloro-1-propene (GC analysis: 89.4% purity; water (KF): 0.45%) in a 2 liter jacketed reaction vessel with stirrer and reflux condenser. Sodium thiocyanate (165.46 g) (98% purity) is then added, with stirring. The mixture is then heated to 80° C., stirred for two hours at the said temperature, and cooled back to 70° C., and 500 ml of water are added. The organic phase is separated off at room temperature. This gives 512.4 g of organic phase, which according to GC analysis comprises 44.2 percent by area of 2,3-dichloro-1-propene, 20 percent by area of 2-chloroallyl thiocyanate of the formula (I) and 27.9 percent by area of 2-chloroallyl isothiocyanate of the formula (II).

This organic phase is distilled at 250 mbar until the bath temperature reaches 75° C. This gives 221.2 g of distillate with, according to GC analysis, 217.8 g of 2,3-dichloro-1-propene, which can be returned to the process.

The amount of residue after distillation is 288.7 g and according to GC analysis is composed of 17.8 percent by area of 2-chloroallyl thiocyanate of the formula (I) and of 64.4 percent by area of 2-chloroallyl isothiocyanate of the formula (II), giving a yield of 89% of theory, based on sodium thiocyanate.

Example 3

Technical-grade 2,3-dichloro-1-propene (495.4 g) (GC analysis: 89.6% purity; water (KF): 0.45%) is used as initial charge in a 2-liter jacketed reaction vessel with stirrer and reflux condenser, and is heated to 70° C. At this temperature, 155.35 g of ammonium thiocyanate (98% purity) are added in two portions, with stirring. The mixture is then heated to 80° C., and is stirred for two hours at the said temperature, and cooled back to 70° C., and 500 ml of water are added. The organic phase is separated off at room temperature. This gives 514.9 g of organic phase, which according to GC analysis comprises 58.8 percent by area of 2,3-dichloro-1-propene, 13.8 percent by area of 2-chloroallyl thiocyanate of the formula (I) and 19.05 percent by area of 2-chloroallyl isothiocyanate of the formula (II). This gives a yield of 99% of theory, based on reacted 2,3-dichloro-1-propene.

Example 4

Technical-grade 2,3-dichloro-1-propene (495.4 g) (GC analysis: 89.6% purity; water (KF): 0.45%) is used as initial charge in a 2-liter jacketed reaction vessel with stirrer and reflux condenser, and is heated to 70° C. At this temperature, 220.55 g of sodium thiocyanate (98% purity) are added in two portions, with stirring. The mixture is then heated to 80° C., stirred for two hours at the said temperature, and cooled back to 70° C., and 500 ml of water are added. The organic phase is separated off at room temperature. This gives 548.7 g of organic phase, which according to GC analysis comprises 28.3 percent by area of 2,3-dichloro-1-propene, 27.05 percent by area of 2-chloroallyl thiocyanate of the formula (I) and 37.1 percent by area of 2-chloroallyl isothiocyanate of the formula (II). This gives a yield of 99% of theory, based on sodium thiocyanate.

Example 5

Technical-grade 2,3-dichloro-1-propene (496.5 g) (GC analysis: 89.4% purity; water (KF): 0.45%) is used as initial charge in a 2-liter jacketed reaction vessel with stirrer and reflux condenser, and is heated to 70° C. At this temperature, 165.46 g of sodium thiocyanate (98% purity) are added in two portions, with stirring. The mixture is then heated to 80° C., stirred for two hours at the said temperature, and cooled back to 70° C., and 340 ml of water are added. The organic phase is separated off at 70° C. This gives 523.4 g of organic phase, which according to GC analysis comprises 48.4 percent by area of 2,3-dichloro-1-propene, 18.55 percent by area of 2-chloroallyl thiocyanate of the formula (I) and 23.9 percent by area of 2-chloroallyl isothiocyanate of the formula (II). This gives a yield of 81% of theory, based on sodium thiocyanate.

The invention claimed is:
1. A process for producing 2-chloroallyl isothiocyanate of formula (II),

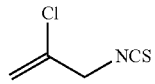
(II)

comprising reacting 2,3-dichloro-1-propene of formula (III),

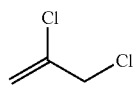
(III)

with a thiocyanate of formula (IV), $M(SCN)_n$ (IV), in which
M is a metal cation or an ammonium group
and
n is from 1 to 4, as appropriate for a charge number of the cation,
in the presence of a phase transfer catalyst of formula (V),

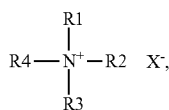
(V)

in which moieties
$R^1$, $R^2$, $R^3$ and $R^4$ are mutually independently hydrogen, $C_1$-$C_{24}$-alkyl, benzyl or $C_6$-$C_{10}$-aryl, the latter optionally substituted by halogen, $C_1$-$C_6$-alkyl, $C_1$-$C_6$-alkoxy, $C_1$-$C_6$-alkylamino, $C_1$-$C_6$-dialkylamino, hydroxy or phenyl
and
X is an anion,
without diluent or in the presence of up to 15 percent by weight, based on 2,3-dichloropropene of formula (III) and simultaneously in the presence of an excess of from 10 to 200 mol percent of 2,3-dichloro-1-propene of formula (III) based on a thiocyanate of formula (IV).

2. The process according to claim 1, wherein the amount used of a diluent is up to 10 percent by weight, based on the 2,3-dichloropropene of formula (III).

3. The process according to claim 1, where the amount used of a diluent is up to 5 percent by weight, based on the 2,3-dichloropropene of formula (III).

4. The process according to any of claim 1, where said reacting proceeds at a temperature range from 50 to 100° C.

5. A process for producing 2-chloroallyl isothiocyanate of formula (II),

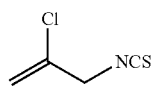
(II)

comprising reacting 1,2,3-trichloropropane of formula (VI)

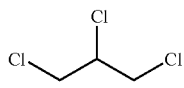
(VI)

with a base and then reacting resultant 2,3-dichloro-1-propene of formula (III)

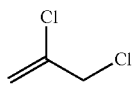
(III)

with a thiocyanate of formula (IV), $$M(SCN)_n \quad (IV),$$

in which

M is a metal cation or an ammonium group and n is from 1 to 4, as appropriate for a charge number of the cation, in the presence of a phase transfer catalyst of formula (V),

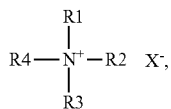
(V)

in which moieties $R^1$, $R^2$, $R^3$ and $R^4$ are mutually independently hydrogen, $C_1$-$C_{24}$-alkyl, benzyl or $C_6$-$C_{10}$-aryl, the latter optionally substituted by halogen, $C_1$-$C_6$-alkyl, $C_1$-$C_6$-alkoxy, $C_1$-$C_6$-alkylamino, $C_1$-$C_6$-dialkylamino, hydroxy or phenyl and X is an anion, without diluent or in the presence of up to 15 percent by weight, based on 2,3-dichloropropene of formula (III) and simultaneously in the presence of an excess of from 10 to 200 mol percent of 2,3-dichloro-1-propene of formula (III) based on a thiocyanate of formula (IV).

6. The process according to claim 1, wherein

M is $Na^+$ or $NH_4^+$, n is 1, $R^1$, $R^2$, $R^3$ and $R^4$ are mutually independently hydrogen, $C_1$-$C_{24}$-alkyl, benzyl or phenyl and X is an anion from the group of chloride, bromide, hydrogensulphate or hydroxide.

\* \* \* \* \*